United States Patent
Lee et al.

(10) Patent No.: US 8,169,124 B2
(45) Date of Patent: May 1, 2012

(54) PHYSICAL/BIOCHEMICAL SENSOR USING PIEZOELECTRIC MICROCANTILEVER AND MANUFACTURING METHOD THEREOF

(75) Inventors: Jai Chan Lee, Seoul (KR); Sang Hun Shin, Gyeonggi-do (KR)

(73) Assignee: Sungkyunkwan University Foundation for Corporate Collaboration (KR)

( * ) Notice: Subject to any disclaimer, the term of this patent is extended or adjusted under 35 U.S.C. 154(b) by 88 days.

(21) Appl. No.: 12/579,660

(22) Filed: Oct. 15, 2009

(65) Prior Publication Data

US 2010/0033058 A1    Feb. 11, 2010

Related U.S. Application Data

(63) Continuation-in-part of application No. PCT/KR2009/000868, filed on Feb. 24, 2009.

(30) Foreign Application Priority Data

Feb. 29, 2008 (KR) .................. 10-2008-0019031

(51) Int. Cl.
*H01L 41/08* (2006.01)
(52) U.S. Cl. .................. 310/331; 310/321; 310/312
(58) Field of Classification Search ........... 310/330–332
See application file for complete search history.

(56) References Cited

U.S. PATENT DOCUMENTS

| | | | |
|---|---|---|---|
| 5,856,722 A * | 1/1999 | Haronian et al. | 310/321 |
| 6,575,020 B1 * | 6/2003 | de Charmoy Grey et al. | 73/54.23 |
| 7,291,466 B2 * | 11/2007 | Su et al. | 435/6.19 |
| 7,425,749 B2 * | 9/2008 | Hartzell et al. | 257/414 |
| 7,583,012 B2 * | 9/2009 | Nakashio et al. | 310/358 |
| 7,904,158 B2 * | 3/2011 | Stegemann et al. | 607/18 |

FOREIGN PATENT DOCUMENTS

| | | |
|---|---|---|
| JP | 01209354 A | 8/1989 |
| JP | 04370742 A | 12/1992 |
| KR | 20050095964 A | 10/2005 |
| KR | 20050096469 A | 10/2005 |
| KR | 20060025353 A | 3/2006 |

OTHER PUBLICATIONS

International Search Report, PCT/KR2009/000868.

* cited by examiner

*Primary Examiner* — Mark Budd
(74) *Attorney, Agent, or Firm* — Cantor Colburn LLP

(57) ABSTRACT

The present invention discloses a physical/biochemical sensor using a multisized piezoelectric microcantilever resonator array which enables to quantitatively and simultaneously analyze a mass loading effect and a surface stress change effect and a manufacturing method thereof. In the physical/biochemical sensor using the multisized piezoelectric microcantilever resonator array, a plurality of piezoelectric microcantilever resonators having different sizes is arrayed so as to quantitatively and discriminately analyze a surface stress change as well as a sensor surface mass change induced by an adsorbed sensing-target material occurring in a sensing process. Thus, the mass loading effect and the surface stress change effect can be quantitatively and simultaneously analyzed.

11 Claims, 5 Drawing Sheets

PHYSICAL/BIOCHEMICAL SENSOR USING PIEZOELECTRIC MICROCANTILEVER AND MANUFACTURING METHOD THEREOF

CROSS-REFERENCES TO RELATED APPLICATIONS

This is a continuation-in-part of International Application No. PCT/KR2009/000868 filed on Feb. 24, 2009, which claims the benefit of Korean Patent Application No. 2008-019031, filed on Feb. 29, 2008, in the Korean Patent Office. The disclosures of said applications are incorporated by reference herein.

FIELD OF THE INVENTION

The present invention relates to a physical/biochemical sensor using a multisized piezoelectric microcantilever resonator array and a manufacturing method thereof; and, more particularly, the present invent relates to a physical/biochemical sensor using a multisized piezoelectric microcantilever resonator array, which enables a simultaneous and quantitative analysis of both an surface stress change effect and a mass loading effect due to adsorption of a sensing-target material by measuring a resonant frequency shift obtained during a sensing process, and thus can be used for analyzing a sensing-target material in various application fields, and to a manufacturing method thereof.

BACKGROUND OF THE INVENTION

The ultimate goal of the modern scientific technology development is to improve the quality of human life. Especially, in the fields of biotechnology and environmental engineering, various researches have been actively conducted to predict a disease or diagnose a disease at an early stage prior to starting the treatment and to efficiently control various kinds of problems that may directly affect the human life span.

As examples of such research trend, the research and developments have been made for a human body biomarker for detecting a harmful substance or diagnosing a disease, and a super-microscopic precision sensor system for detecting the presence of a sensing-target material such as a pathogenic organism, or the occurrence of a certain biochemical reaction in a fast and simple manner. When a biochemical substance and a harmful pollutant to be sensed, which exist in air, aquatic environment or the human body, are present in a very low concentration, there are many drawbacks to be overcome in order to analyze them by a conventional analysis method. That is, a high-cost and large-scale analyzing apparatus is required for extraction, concentration and analysis of a sample and it takes a great amount of time for pre-treating a sample. In order to analyze the sensing-target material on a real-time basis without having to perform the sample pre-process such as the sample extraction and concentration, the sensitivity of a sensor device used in the analysis needs to be high enough to detect a mass at a single-molecule level.

As one of such sensors, a microcantilever integrated with a piezoelectric driving component can be self-driven by an AC electric field and can quickly read a great change in an AC signal caused by a piezoelectric effect at a resonant frequency point through an electric measurement. Research reports related to this have been already reported by many other researchers, including the patent applications and the journals filed and published by the present inventors' research group.

In an actual application for detecting a sensing-target material, a microcantilever resonator sensor operated with a resonant frequency using a piezoelectric mechanism or another driving principle outputs a sensing signal in the form of a resonant frequency shift of a cantilever with respect to a mass change on a cantilever surface that occurs during a sensing process, and analyzes it to give a result. To implement a wider range of application and a more accurate analysis, it is desirable to use an array-type device having an array of a plurality of cantilevers rather than to use a single cantilever. Meanwhile, the resonant frequency of the cantilever decreases or increases due to a change in the surface stress as well as due to a change in the surface mass during the sensing process. However, when a single cantilever or an array-type device having an array of a plurality of same-sized cantilevers is used, a mass loading effect and a surface stress change effect occurring during the sensing process cannot be distinguished when a resonant frequency change as a sensing signal is analyzed. Although the degree of mechanical bending of the cantilever due to the surface stress change can be measured and analyzed by an optical method, it is difficult to discriminately analyze the mass loading effect and the surface stress change effect in case of using the resonant frequency shift as a primary sensing signal, since the mass loading effect and the surface stress effect are simultaneously exerted.

BRIEF SUMMARY OF THE INVENTION

In view of the foregoing, the present invention provides a physical/biochemical sensor using a multisized piezoelectric microcantilever resonator array, which enables a quantitative and simultaneous analysis of both a surface stress change effect and a mass loading effect induced by adsorption of a sensing-target material.

In accordance with one aspect of the present invention, there is provided a physical/biochemical sensor using a multisized piezoelectric microcantilever resonator array, in which a plurality of piezoelectric microcantilever resonators having different sizes is arrayed so as to quantitatively analyze a surface stress change as well as a surface mass change induced by an adsorption of a sensing-target material that occurs during a sensing process while discriminating between the two changes.

Further, the multisized piezoelectric microcantilever resonator array includes:

a plurality of silicon nitride layer cantilevers formed on a silicon substrate, the silicon nitride layer cantilevers being arrayed in a manner that their lengths are gradually reduced;

a silicon oxide layer formed on each of the silicon nitride layer cantilevers;

a lower electrode formed in a preset size on the silicon oxide layer;

a piezoelectric driving thin layer for piezoelectric driving, formed on the lower electrode;

an insulating layer for an inter-electrode insulation, formed on the lower electrode and on a part of the piezoelectric driving thin layer;

an upper electrode formed on the insulating layer and on the piezoelectric driving thin layer; and an electrode line for applying an electric field to drive a device, connected to the upper electrode and the lower electrode.

In accordance with another aspect of the present invention, there is provided a method for manufacturing a physical/biochemical sensor using a multisized piezoelectric microcantilever resonator array, the method including:

(a) depositing a silicon nitride layer cantilever on each of a top and a bottom of a silicon substrate;

(b) depositing a silicon oxide layer on the upper silicon nitride layer cantilever;

(c) forming a lower electrode including a junction layer on the entire surface of the silicon oxide layer;

(d) forming a piezoelectric driving thin layer for piezoelectric driving on the entire top surface of the lower electrode;

(e) etching a part of the formed piezoelectric driving thin layer to form a multisized piezoelectric driving thin layer material array integrated in the multisized piezoelectric microcantilever resonator array sensor;

(f) etching a part of the lower electrode below the multisized piezoelectric driving thin layer material array to form a multisized lower electrode array, and an electrode line and a pad for applying a driving voltage, integrated in the multisized microcantilever resonator array;

(g) forming an insulating layer for insulation between an upper electrode and the lower electrode on a part of the multisized lower electrode array and the multisized piezoelectric driving thin layer material array;

(h) forming a multisized upper electrode array, and an electrode line and a pad for applying a driving voltage on the insulating layer and on the multisized piezoelectric driving thin layer material array;

(i) removing a part of the lower silicon nitride layer cantilever;

(j) etching the silicon substrate exposed after the step (i); and (k) removing a part of the upper silicon nitride layer of the device wherein the silicon substrate is etched in the step (j) to form a multisized piezoelectric microcantilever resonator array sensor.

As described, a physical/biochemical sensor using a multisized piezoelectric microcantilever resonator array in accordance with the present invention has an advantage in that it is capable of discriminately analyzing a surface stress change as well as a surface mass change of the sensor induced by an adsorbed sensing-target material which occurs during various sensing processes. That is, since it is feasible to rapidly respond to a concentration of an extremely small amount of a sensing-target material from the outside and thus to conduct an immediate detection via the resonant frequency shift, it has a high response speed and a high sensitivity. Further, since the effect of the surface stress change in the sensing process in addition to the increase of the surface-adsorbed mass by a biochemical reaction can be recognized, a wider range of information from the sensing results can be acquired and more accurate sensing results can be obtained.

Moreover, when a sensor platform in accordance with the present invention is applied to a biochemical field, not only a presence or absence of a sensing-target material can be determined but also a reaction between the sensing material and the sensing-target material and a reaction behavior between the sensing-target materials can be investigated directly or indirectly.

Meanwhile, when the sensor platform in accordance with the present invention is used as a physical sensor for measuring a thickness of a thin film in a deposition process for forming thin films of various materials instead of a conventional quartz crystal microbalance (QCM) sensor, the surface stress effect can be analyzed by electrically analyzing only a resonant frequency signal obtained from the multisized piezoelectric microcantilever resonator array, so that more accurate information upon the thickness of the deposited thin film can be obtained and also mechanical characteristics of the thin material can be simultaneously analyzed.

DETAILED DESCRIPTION OF THE INVENTION

Hereinafter, a physical/biochemical sensor using a multisized piezoelectric microcantilever resonator array and a manufacturing method thereof will be described in detail in accordance with an embodiment of the present invention with reference to the accompanying drawings.

Figure 1:
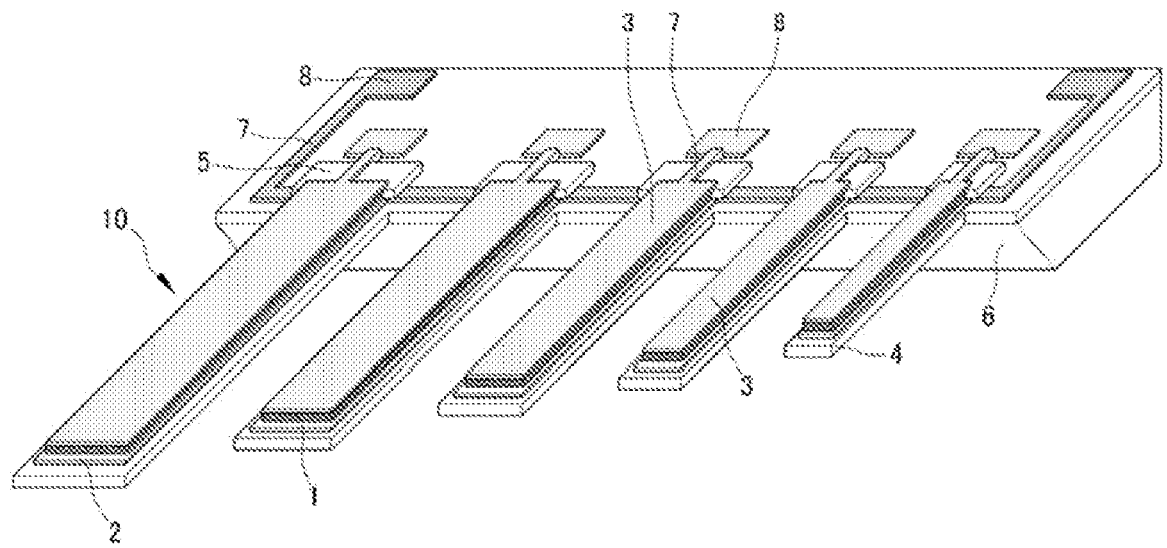
FIG. 1 is a schematic configuration view of a physical/biochemical sensor using a multisized piezoelectric microcantilever resonator array in accordance with an embodiment of the present invention.
Figure 2:
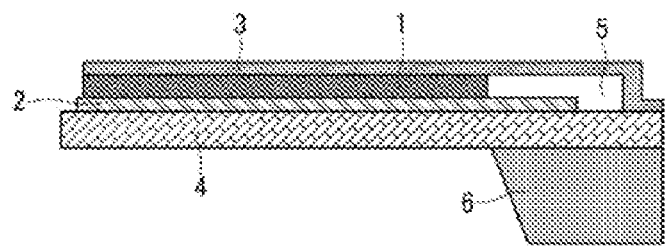
FIG. 2 is a cross sectional view of the physical/biochemical sensor using the multisized piezoelectric microcantilever resonator array.
Figure 3A:
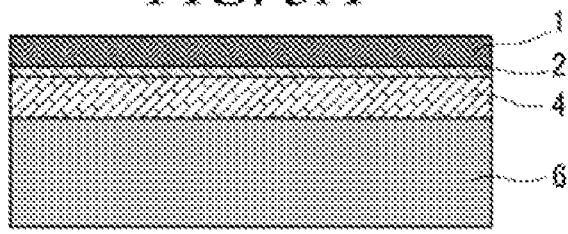
FIGS. 3A to 3E provide cross sectional state views to describe a manufacturing process of the physical/biochemical sensor using the multisized piezoelectric microcantilever resonator array.
Figure 3B:
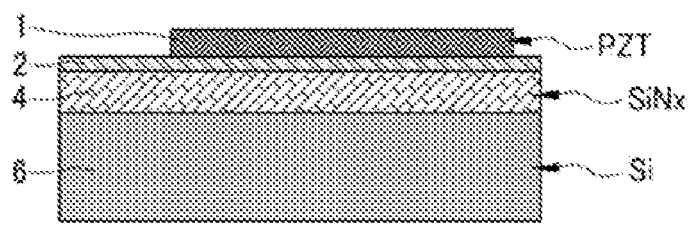
Figure 3C:
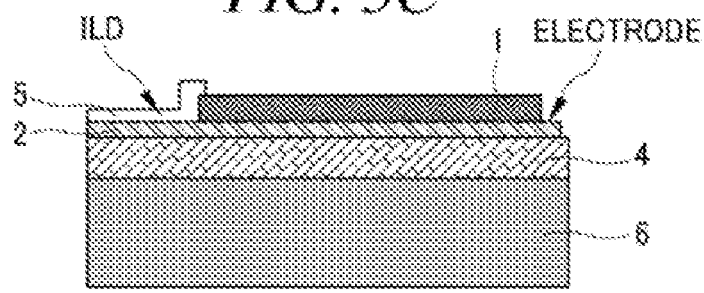
Figure 3D:
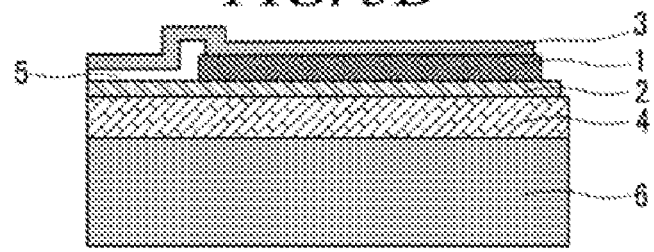
Figure 3E:
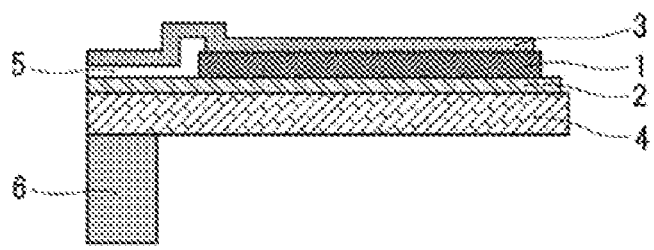
Figure 4A:
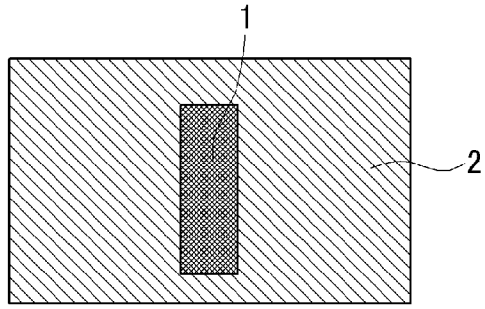
FIGS. 4B to 4E present a plane view (top view) to describe the manufacturing process of the physical/biochemical sensor using the multisized piezoelectric microcantilever resonator array.
Figure 4B:
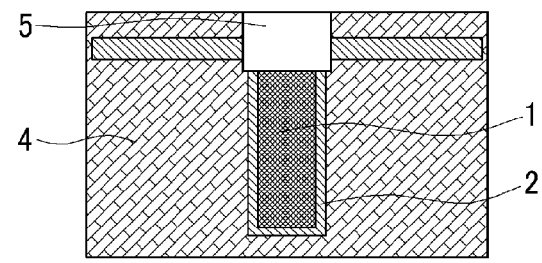
Figure 4C:
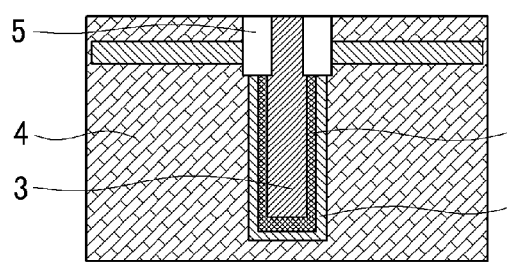
Figure 4D:
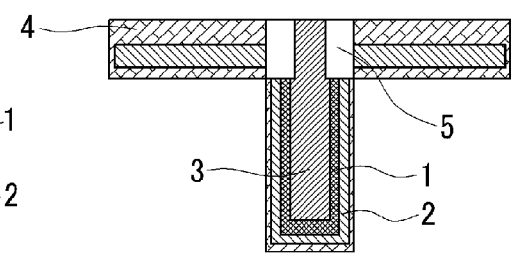
Figure 5:
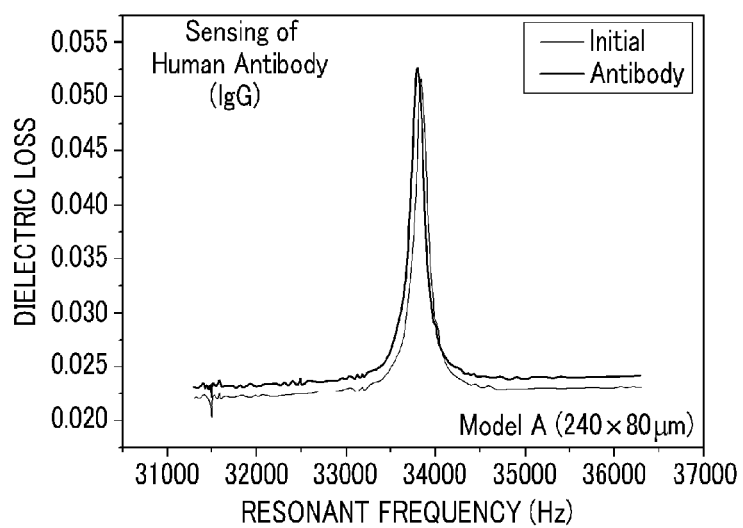
FIGS. 5 to 9 are graphs showing the resonant frequency shift in each of piezoelectric microcantilever resonator arrays, respectively.
Figure 6:
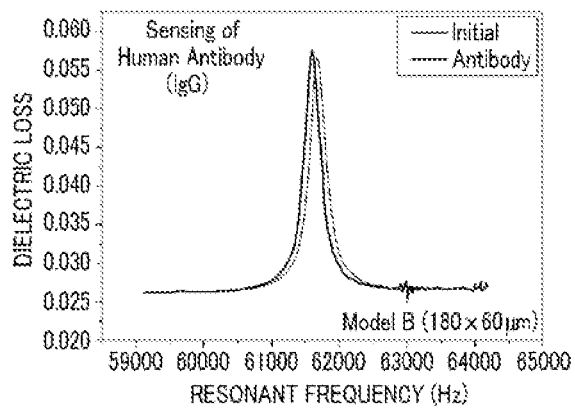
Figure 7:
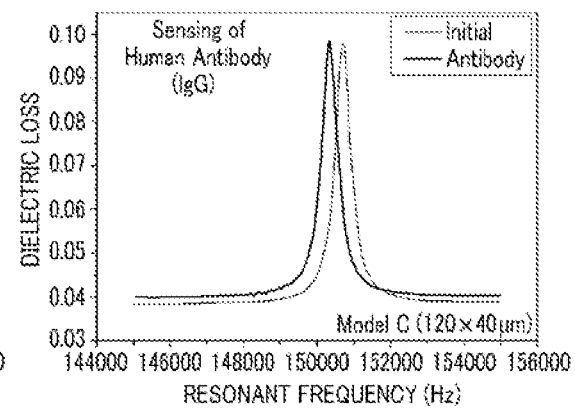
Figure 8:
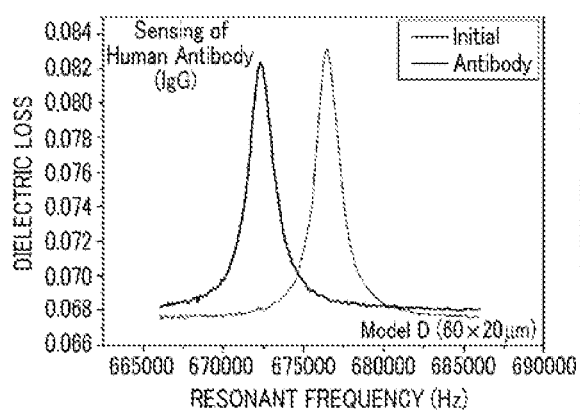
Figure 9:
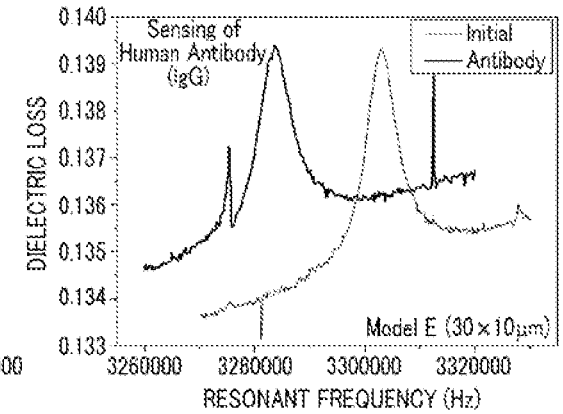
Figure 10:
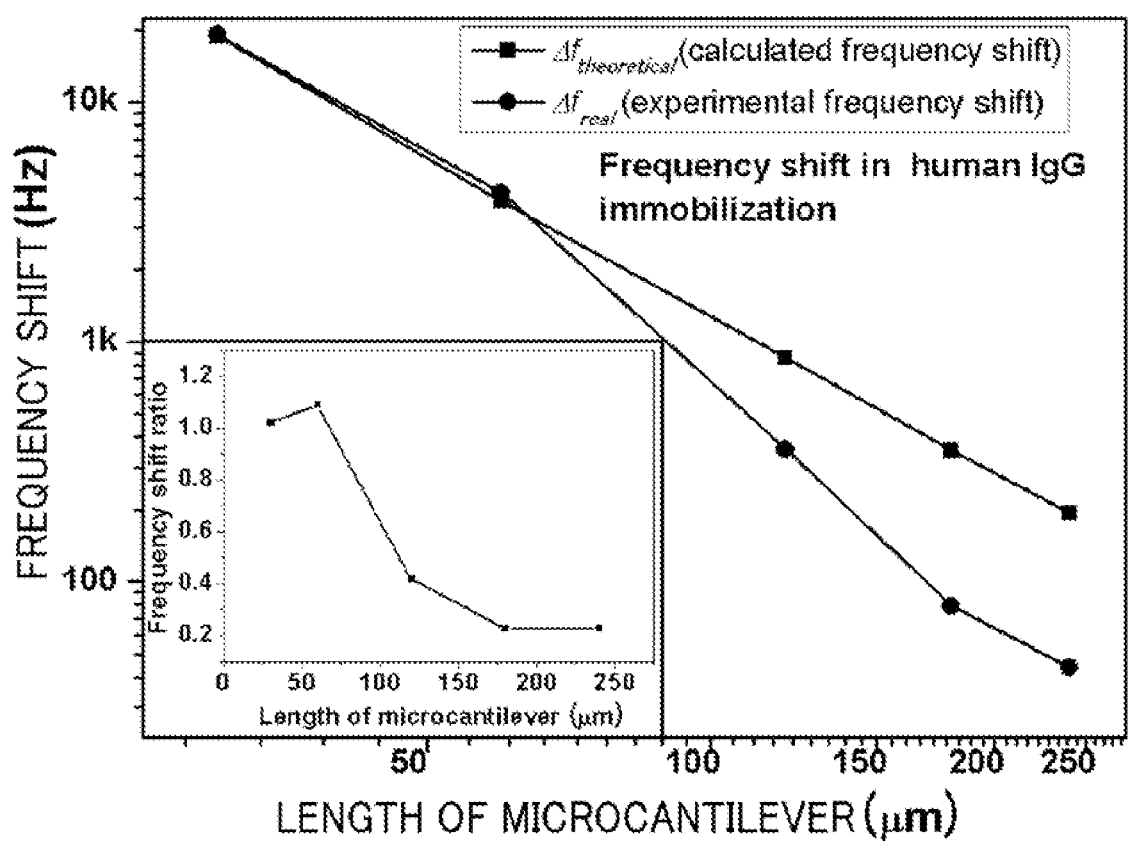
FIG. 10 is a graph indicating a frequency shift obtained by the physical/biochemical sensor using the multisized piezoelectric microcantilever resonator array as a function of lengths of piezoelectric microcantilever resonators.

FIG. 1 is a schematic configuration view of the physical/biochemical sensor using the multisized piezoelectric microcantilever resonator array in accordance with the embodiment of the present invention, and FIG. 2 is a cross sectional view of the physical/biochemical sensor using the multisized piezoelectric microcantilever resonator array. FIGS. 3A to 3E are cross sectional state views to describe a manufacturing process of the physical/bio-chemical sensor using the multisized piezoelectric micro-cantilever resonator array. FIG. 4 depicts plane views to describe the manufacturing process of the physical/bio-chemical sensor using the multisized piezoelectric micro-cantilever resonator array, and FIGS. 5 to 9 are graphs showing a resonant frequency shift of each piezoelectric microcantilever resonator array. FIG. 10 is a graph indicating a frequency shift obtained by the physical/bio-chemical sensor using the multisized piezoelectric micro-cantilever resonator array as a function of lengths of piezoelectric microcantilever resonators.

As illustrated, the physical/biochemical sensor using the multisized piezoelectric microcantilever resonator array has a configuration in which a plurality of piezoelectric microcantilever resonators 10 having different sizes are arrayed. That is, the piezoelectric microcantilever resonators 10 are arrayed in a manner that they are 2-dimensionally and gradually scaled down.

Each of the piezoelectric microcantilever resonators 10, constituting the microcantilever resonator array and having the different sizes, includes: a supporting layer 4 formed on a silicon substrate 6; a lower electrode 3 formed on the supporting layer 4 in a predetermined size; a piezoelectric driving thin layer 1 for piezoelectric driving, formed on the lower electrode 3; an insulating layer 5 for inter-electrode insulation, formed on the lower electrode 2 and on a part of the piezoelectric driving thin layer 1; an upper electrode 3 formed on the insulating layer 5 and on the piezoelectric driving thin layer 1; and an electrode line 7 and a pad 8 connected to the upper electrode and the lower electrode so as to apply an electric field for driving a device. Here, the supporting layers 4 of the respective resonators 10 are arrayed in a manner that their lengths are gradually reduced.

The supporting layers 4 includes a plurality of a silicon nitride layer cantilevers formed on the silicon substrate 6, which are arrayed in a manner that their lengths are gradually reduced, and silicon oxide layers formed on each of the silicon nitride layer cantilevers.

In the piezoelectric microcantilever resonator 10, a piezoelectric material is used as a thin layer material for piezoelectric driving. Such piezoelectric materials are what use a principle that a potential difference (voltage) is generated when a pressure is applied to a certain crystal while a physical displacement occurs when a potential difference (voltage) is reversely applied thereto. The piezoelectric material is mainly classified into nitrides and oxides. Aluminum nitride (AlN) is typically used as the nitride, and, as the oxide, zinc oxide (ZnO) which is a piezoelectric material without lead, or Pb(Zr,Ti)O$_3$ (lead zirconium titanate, hereinafter, simply referred to as PZT) which is a piezoelectric material with lead is typically used.

The insulating layer 5 is formed by a photolithography process using a patternable material such as photosensitive polyimides. A fundamental resonant frequency and a resonant frequency shift of a piezoelectric driving device are indicated by a variation of an electric signal such as complex impedance, which is measured by an impedance analyzer incorporated in a sensor module. Thus, the physical/biomechanical sensor, using the multisized piezoelectric microcantilever resonator array which includes the plurality of piezoelectric microcantilever resonators 10 arrayed with being 2-dimensionally and gradually scaled down, measures a resonant frequency value of the device by detecting frequency using an oscillator and a frequency counter implemented on a circuit, and determines a presence or absence of a sensing-target material by measuring and analyzing all resonant frequencies of the piezoelectric microcantilevers included in the multisized microcantilever resonator array 10, wherein the resonant frequencies are changed by a reaction between a sensing material layer of the sensor and the sensing-target material after the device is exposed to a measuring environment.

The fundamental resonant frequency value of the piezoelectric microcantilever resonator 10 in the present invention increases in reciprocal proportion to the square of a device length, and excellent sensitivity can be attained in comparison to the case that a high resonant frequency value is obtained by reducing the size of the device. Especially, in order to detect a microscopic material having a molecule-level mass, a device capable of sensing a small mass in or below a femtogram regime is required. Accordingly, among the silicon nitride layer cantilevers having various sizes which are included in the multisized piezoelectric microcantilever resonator array 10, a small silicon nitride layer cantilever showing a higher sensitivity to an increase of a surface mass which occurs during the sensing process of the sensing-target material is desirably set to have a length and a width of about 30 μm and about 10 μm, respectively.

For example, when the piezoelectric microcantilever resonators 10 having five different sizes are integrated, the size (length, width and thickness) of each resonator is as follows.

A: 240 μm (length), 80 μm (width), 2.3 μm (thickness)
B: 180 μm (length), 60 μm (width), 2.3 μm (thickness)
C: 120 μm (length), 40 μm (width), 2.3 μm (thickness)
D: 60 μm (length), 20 μm (width), 2.3 μm (thickness)
E: 30 μm (length), 10 μm (width), 2.3 μm (thickness)

Desirably, the upper electrode, the lower electrode, the piezoelectric driving thin layer and the supporting layer (silicon nitride layer cantilever+silicon oxide layer) are designed to have thicknesses of about 0.1 μm, 0.15 μm, 0.5 μm and 1.55 μm (1.2 μm+0.35 μm), respectively.

Since the piezoelectric microcantilever resonator 10 having the smallest length of about 30 μm has a sufficiently large spring constant, it tends to be insensitive to a stress change on a cantilever surface which occurs in the sensing process. On the other hand, since the large piezoelectric microcantilever resonator 10 having the length of about 240 μm has a small spring constant, it is sensitive to both a surface mass increase and a surface stress change that occur in the sensing process.

A change of the spring constant k ($k_{Theoretical}$) according to the size of the microcantilever resonator 10 can be explained by the following equation.

$$k = \frac{1}{4} \frac{E * t^2 w}{L^3}$$

In the above equation, E* used to define the spring constant ($k_{Theoretical}$) denotes the Young's Modulus of the microcantilever resonator 10; t, the thickness of the microcantilever resonator; w and L, the width and the length of the microcantilever resonator, respectively. In the present invention, the thicknesses of the microcantilever resonators included in the multisized microcantilever resonator array are maintained constant. Thus, the thickness t in the above equation is not considered in describing a relationship between the spring constant change and the planar size of the microcantilever resonator 10. Accordingly, the spring constant change depending on the variation of the size of the microcantilever resonator 10 is determined by a ratio (w/L$^3$) of the width to the cube of the length of the microcantilever resonator 10. Further, when the planar size of the microcantilever resonator 10 is 2-dimensionally reduced while the ratio (L/w) of the length to the width thereof is maintained constant, it can be found that the spring constant ($k_{Theoretical}$) of the microcantilever resonator 10 increases in reciprocal proportion to the square of the length.

Among the piezoelectric microcantilever resonators 10 illustrated in the present embodiment, the largest resonator has a length eight times as long as that of the smallest one. Consequently, the smallest resonator has a spring constant of about 64 times as great as that of the largest one.

In order to discriminately analyze a surface mass loading effect and a surface stress change effect in an application of the sensor, it may be desirable to design a length difference between the piezoelectric microcantilevers 10 to be at least three times so that the spring constants of a small microcantilever and a large microcantilever have a difference of at least 10 times.

The manufacturing process of the physical/biochemical sensor using the multisized piezoelectric microcantilever resonator array is described as follows with reference to FIGS. 3 and 4.

The manufacturing process includes the steps of (a) depositing a silicon nitride layer cantilever on each of a top and a bottom of a silicon substrate; (b) forming a supporting layer 4 by depositing a silicon oxide layer on the upper silicon nitride layer cantilever; (c) forming a lower electrode 2 including a junction layer on the entire top surface of the silicon oxide layer; (d) forming a piezoelectric driving thin layer 1 for piezoelectric driving on the entire top surface of the lower electrode 2; (e) etching a part of the formed piezoelectric driving thin layer 1 to form a multisized piezoelectric driving thin layer material array integrated in the multisized piezoelectric microcantilever resonator array sensor; (f) etching a part of the lower electrode 2 below the multisized piezoelectric driving material array to form a multisized lower electrode array, and an electrode line 7 and a pad 8 for applying a driving voltage, integrated in the multisized piezoelectric microcantilever resonator array sensor; (g) forming an insulating layer 5 for insulating between an upper electrode and the lower electrode on a part of each of the multisized lower electrode array and the multisized piezoelectric driving thin layer material array; (h) forming a multisized upper electrode array, and an electrode line 7 and a pad 8 for applying a driving voltage, on the insulating layer 5 and on the multisized piezoelectric driving thin layer material array; (i) removing a part of the lower silicon nitride layer cantilever; (j) etching the silicon substrate 6 exposed after the step (i); and (k) removing a part of the upper silicon nitride layer of the device wherein the silicon substrate 6 is etched in the step (j) to thereby form a multisized piezoelectric microcantilever resonator array sensor.

The manufacturing process may further include a step (l) of forming a sensing layer for sensing the sensing-target material after the step (k).

The step (l) may involve depositing a gold thin film on the microcantilever surface, forming a self-assembled monolayer by using a gold-thiol reaction, and immobilizing a sensing material suitable for the sensing-target material, so as to form a sensing material layer for sensing a biomaterial. Alternatively, for an application as a chemical sensor, the step (l) may include forming a sensing material layer by inkjet-printing, spin-coating or dip-coating a solution containing a polymer material to which the sensing-target material can be bonded, on the microcantilever surface.

FIGS. 5 to 9 show resonant frequency shifts in the multisized piezoelectric microcantilever resonators 10 having five different sizes, which were obtained after a series of steps of depositing a gold thin film on a rear surface of each multisized piezoelectric microcantilever resonator 10, forming a self-assembled monolayer by a gold-alkanethiol reaction and immobilizing a human antibody by using biotin, streptavidin, and the like. The small resonator(s) has a very high resonant frequency, and its sensitivity to a loaded mass is very high. Accordingly, a frequency decrease due to the immobilization of the human antibody (IgG) was conspicuous. Meanwhile, since the large resonator(s) has a smaller fundamental resonant frequency and a lower sensitivity to a mass compared to the small one(s), the large resonator(s) showed a comparatively smaller decrease in the frequency than the results of the small size resonator(s) which were simultaneously obtained.

FIG. 10 shows a frequency shift obtained in each of the multisized piezoelectric microcantilever resonators 10 as a function of a cantilever length, according to the embodiments depicted in FIGS. 5 to 9. In FIG. 10, a graph illustrated by a line with black squares indicates a theoretical frequency shift which is expected due to a surface mass increase when the human antibody (IgG) is immobilized using the multisized piezoelectric micro-cantilever resonator array sensor, and a graph illustrated by a line with circles indicates a frequency shift obtained in an actual experiment.

As can be seen from the graphs, the piezoelectric microcantilever resonator 10 having the length of about 30 μm was found to be hardly affected by a surface stress induced during the sensing process. Accordingly, in implementing multiple sizes, it is deemed to be desirable as a piezoelectric microcantilever resonator 10 having a property that a frequency shift induced by an adsorbed mass is dominant. However, it may be desirable to use a piezoelectric microcantilever resonator 10 having a smaller size and a high spring constant to be less affected by the surface stress induced during the sensing process. Meanwhile, the piezoelectric microcantilever resonator 10 having the length of 240 μm was found to be greatly affected by the surface stress, so that it is deemed to be desirable as a piezoelectric microcantilever resonator 10 having a property that a frequency shift induced by a surface stress change is dominant.

As described above, by using the physical/biochemical sensor using the multisized piezoelectric microcantilever resonator array in accordance with the present invention, not only the information upon surface-adsorbed mass during the sensing process can be analyzed, but also the surface stress effect can be simultaneously analyzed by comparing an expected frequency shift pattern obtained from a mass sensitivity of each of the multisized piezoelectric microcantilever resonator arrays having their own sizes with a resonant frequency shift pattern obtained in the actual sensing process. That is, more abundant information upon a biochemical reaction between the sensing material formed on the surface of the cantilever and the sensing-target material can be obtained. Therefore, the physical/biochemical sensor using the multisized piezoelectric microcantilever resonator array in accordance with the present invention is capable of quickly and accurately detecting a presence or absence of various kinds of sensing-target materials in an extremely small amount, and also capable of simultaneously and discriminately analyzing a surface stress effect when the sensing material formed on the surface of the cantilever reacts with the various kinds of sensing-target materials, thus improving an ability to discriminate between the sensing-target materials in sensing results.

While the invention has been shown and described with reference to the above-described embodiments, the present invention is not limited thereto, and it would be understood by those skilled in the art that various changes and modification may be made without departing form the scope of the invention as claimed in the following claims. Thus, it shall be understood that all modifications and embodiments conceived from the meaning and scope of the claims and their equivalents are included in the scope of the present invention.

What is claimed is:

1. A physical/biochemical sensor having a multisized piezoelectric microcantilever resonator array, the multisized piezoelectric microcantilever resonator array comprising a plurality of piezoelectric microcantilever resonators having different sizes so as to quantitatively and discriminately analyze a surface stress change as well as a mass change on a sensor surface induced by an adsorption of a sensing-target material during a sensing process.

2. The physical/biochemical sensor of claim 1, wherein each of the piezoelectric microcantilever resonators includes:
   a silicon nitride layer cantilever formed on a silicon substrate, the silicon nitride layer cantilevers having gradually-reduced lengths;
   a silicon oxide layer formed on each of the silicon nitride layer cantilever;
   a lower electrode formed in a preset size on the silicon oxide layer;
   a piezoelectric driving thin layer formed on the lower electrode;
   an upper electrode formed on the piezoelectric driving thin layer;

an insulating layer which provides insulation between the upper and lower electrodes; and an electrode line connected to the upper electrode and the lower electrode, the electric field being applied through the electrode line to drive the piezoelectric microcantilever resonator.

3. The physical/biomechanical sensor of claim 2, wherein the widths of the silicon nitride layer cantilevers are reduced at the same ratio as the reduction ratio of the lengths.

4. The physical/biomechanical sensor of claim 3, wherein the thicknesses of the silicon nitride layer cantilevers are maintained constant.

5. The physical/biomechanical sensor of claim 2, wherein the insulating layer comprises polyimide.

6. The physical/biochemical sensor of claim 2, wherein the piezoelectric driving thin layer is formed of a piezoelectric material for piezoelectric driving in the piezoelectric microcantilever resonator.

7. The physical/biochemical sensor of claim 2, wherein the longest piezoelectric microcantilever resonator has a length at least three times that of the shortest piezoelectric microcantilever resonator.

8. A method for fabricating a physical/biochemical sensor of claim 1, the method comprising:
 (a) depositing a silicon nitride layer cantilever on each of a top and a bottom of a silicon substrate to form an upper silicon nitride layer cantilever and a lower silicon nitride layer cantilever;
 (b) depositing a silicon oxide layer on the upper silicon nitride layer cantilever;
 (c) forming a lower electrode including a junction layer on the surface of the silicon oxide layer;
 (d) forming a piezoelectric driving thin layer for piezoelectric driving on the top surface of the lower electrode;
 (e) etching a part of the formed piezoelectric driving thin layer to form a multisized piezoelectric driving thin layer material array integrated in the multisized piezoelectric microcantilever resonator array sensor;
 (f) etching a part of the lower electrode below the multisized piezoelectric driving thin layer material array to form a multisized lower electrode array, and an electrode line and a pad for applying a driving voltage, integrated in the multisized microcantilever resonator array;
 (g) forming an insulating layer for insulation between an upper electrode and the lower electrode on a part of the multisized lower electrode array and the multisized piezoelectric driving thin layer material array;
 (h) forming a multisized upper electrode array, and the electrode line and the pad for applying a driving voltage on the insulating layer and on the multisized piezoelectric driving thin layer material array;
 (i) removing a part of the lower silicon nitride layer cantilever;
 (j) etching the silicon substrate exposed after the step (i); and
 (k) removing a part of the upper silicon nitride layer wherein the silicon substrate is etched in the step (j) to form a multisized piezoelectric microcantilever resonator array sensor.

9. The method of claim 8, after the step (k), further comprising a step (l) of forming a sensing layer for detecting a sensing-target material.

10. The method of claim 9, wherein the step (l) includes depositing a gold thin film on the microcantilever surface; forming a self-assembled monolayer by using a gold-thiol reaction; and immobilizing a sensing material suitable for the sensing-target material, so as to form a sensing material layer for detecting a biomaterial.

11. The method of claim 9, wherein the step (l) includes inkjet-printing, spin-coating or dip-coating a solution containing a polymer material to which the sensing-target material can be bonded, on the microcantilever surface, for an application as a chemical sensor.

* * * * *